United States Patent [19]

Eggensperger et al.

[11] Patent Number: 5,496,858
[45] Date of Patent: Mar. 5, 1996

[54] AQUEOUS DISINFECTANT CONCENTRATE AND DISINFECTANT BASED ON ALDEHYDE AND ALCOHOL AND THEIR USE

[75] Inventors: Heinz Eggensperger; Bernd Lower, both of Hamburg; Michael Mohr, Kaltenkirchen; Peter Goroncy-Bermes, Ahrensburg; Rolf Kleinwort, Wedel, all of Germany

[73] Assignee: Reckitt & Colman Inc., Montvale, N.J.

[21] Appl. No.: 179,856

[22] Filed: Jan. 11, 1994

[30] Foreign Application Priority Data

Jan. 15, 1993 [DE] Germany .......................... 43 01 295.7

[51] Int. Cl.$^6$ ........................... A01N 39/00; A01N 47/44
[52] U.S. Cl. ........................... 514/693; 514/694; 514/696; 514/701; 252/106
[58] Field of Search ........................... 514/544, 701, 514/693, 644, 696, 724, 718, 731, 634, 635; 252/606

[56] References Cited

U.S. PATENT DOCUMENTS

| | | | |
|---|---|---|---|
| 3,983,252 | 9/1976 | Buchalter | 424/333 |
| 4,040,977 | 8/1977 | Eggensburger, II et al. | 252/401 |
| 4,946,868 | 8/1990 | Demarne et al. | 514/544 |
| 5,037,989 | 8/1991 | Willingham et al. | 548/213 |
| 5,185,145 | 2/1993 | Eggensburger, I et al. | 424/78.08 |
| 5,234,832 | 8/1993 | Disch et al. | 435/264 |
| 5,250,573 | 10/1993 | Magni | 514/701 |

FOREIGN PATENT DOCUMENTS

| | | |
|---|---|---|
| 0264658 | 4/1988 | European Pat. Off. . |
| 2433836 | 1/1976 | Germany . |

*Primary Examiner*—Shep K. Rose
*Attorney, Agent, or Firm*—Frederick H. Rabin; J. Richard Everett

[57] ABSTRACT

Aqueous disinfectant concentrate which includes succinic dialdehyde, glutaraldehyde and/or formaldehyde, one or more alcohols of limited water miscibility and optionally usual auxiliaries. By diluting with water, a working solution can be prepared from the concentrate. The advantages of the new disinfectant concentrate or disinfectant are the reduced development of odor, an improved material compatibility, an improved microbicidal effectiveness and a clearly increased storage-stability. Furthermore, the activation usual up until now with disinfectants based on aldehyde is superfluous. Preferred application fields are surface and instrument disinfection.

10 Claims, No Drawings

AQUEOUS DISINFECTANT CONCENTRATE AND DISINFECTANT BASED ON ALDEHYDE AND ALCOHOL AND THEIR USE

The invention relates to an aqueous disinfectant concentrate which includes aldehyde and alcohol and optionally additional auxiliaries, a disinfectant producible from it and their use.

After use, medical instruments are usually disinfected by chemical or physical processes. Physical processes such as heat or steam disinfection have admittedly become established in practice, but their general applicability is limited, particularly by the lack of thermal stability of many instruments, e.g. endoscopes. An essential disadvantage of the known chemical processes is, however, their restricted action spectrum against bacteria, fungi and viruses, toxicity and insufficient material compatibility, particularly with the different plastics parts of thermolabile instruments.

To achieve a comprehensive effectiveness which also includes viruses such as e.g. polio viruses and bacteria spores, the active ingredients of choice are aldehydes such as formaldehyde, glutaraldehyde and succinodialdehyde (succinic acid dialdehyde). Products based on aldehydes also give good results as regards material compatibility aspects. The following disadvantages are nevertheless associated with the individual active ingredients.

Formaldehyde has a pungent odor and has recently not been completely accepted because of its sensitizing potential and because of the suspicion of a carcinogenic potential among users.

Glutaraldehyde displays almost the same properties, namely a pungent odor and sensitizing potential; in addition, discoloration of the skin occurs with glutaraldehyde solutions. Furthermore, glutaraldehyde, exactly like formaldehyde, effects a rapid crosslinking of organic material, which makes it more difficult to remove impurities from instruments, the success of disinfection in the inside of endoscopes in particular being put at risk (cf. H. Fleck, Pharmazie (1989), 44, pages 345–347 and S. B. Coghill et al., Lancet I (1989), pages 388–389).

It has therefore been continually attempted in recent years to completely or partially replace glutaraldehyde with succinic acid dialdehyde (also called succinodialdehyde). This occurred primarily because succinic acid dialdehyde crosslinks blood and protein significantly less rapidly, giving penetration into the inside of the possibly contaminated organic material.

In view of lack of stability, however, no free succinic acid dialdehyde was available until recently; rather, succinic acid dialdehyde was offered in the form of its cyclic acetal, dimethoxytetrahydrofuran, from which succinic acid dialdehyde could only partially be released through hydrolysis. A standard commercial disinfectant is based on a mixture of this acetal with further acetals (see e.g. DE-PS 24 33 836) and succinic acid dialdehyde. Dimethoxytetrahydrofuran is however a very volatile substance and therefore easily leads to odor nuisances.

Attempts to formulate the free succinodialdehyde which has been available for a short time (see EP 147 593), which is considerably more easy to tolerate than formaldehyde, glutaraldehyde and dimethoxytetrahydrofuran, to stable concentrations have come to nothing, particularly with high concentrations of the active ingredient in the concentrate (which lead to low application concentrations of the product). Instability was to be observed in two different respects. A reduction of the aldehyde content resulted analytically in some cases and a phase separation in the concentrate and/or in the working solution in other cases.

In the effort to reduce the glutaraldehyde content, a combination of phenoxyethanol with glutaraldehyde, formaldehyde or glyoxal is proposed e.g. in European patent application 0 264 658, although it does obviously require the addition of an alkaline activator to achieve sufficient effectiveness and still relatively high active ingredient concentrations during application.

The object of the invention was therefore to develop an instrument disinfectant concentrate which, compared with the known preparations, shows a reduced odor development, an improved material compatibility, an improved microbicidal effectiveness and a clearly increased shelf life and makes the previously required activation superfluous.

To achieve this object, an aqueous disinfectant concentrate of the type mentioned at the beginning is proposed which is characterized in that it contains, as aldehyde, succinic dialdehyde, glutaraldehyde and/or formaldehyde and, as alcohol, one or more alcohols which have limited miscibility with water which have a water miscibility of 0.1 to 2 wt. % and a vapor pressure at 20° C. of less than 2 mbar.

A further subject of the invention is a disinfectant which is obtainable from the disinfectant concentrate according to the invention on dilution with water, and the use of the disinfectant concentrate according to the invention and of the disinfectant according to the invention.

Preferred versions arise from the dependent claims and the following description.

It was surprisingly found that by adding certain alcohols of limited water miscibility to solutions containing succinic dialdehyde, glutaraldehyde and/or formaldehyde, satisfactorily storage-stable disinfectant concentrates are obtained which show an improved microbicidal effectiveness with improved material compatibility and reduced odor development.

The limited water miscibility of the mono- or polyhydric alcohols is 0.1 to 2 wt. % of the alcohols, relative to the quantity of water. The vapor pressure at 20° C. of the alcohols suitable according to the invention is less than 2 mbar, preferably less than 1 mbar and particularly 0.5 mbar or less. Detailed in the following table are the water miscibility and water solubility and the vapor pressure of some alcohols.

TABLE

| Alcohol | Solubility in water (Wt. %) | Vapor pressure at 20° C. in mbar |
|---|---|---|
| Ethanol | water-miscible | 67 |
| 2-propanol | " | 41.6 |
| 1-propanol | " | 19 |
| Butylglycol | " | <0.8 |
| Butyldiglycol | " | 0.03 |
| Triethylene glycol | " | <0.01 |
| 1,2-propylene glycol | " | <0.1 |
| Polyethylene glycol, 400 | " | <0.1 |
| monophenylglycol ether with 4 mol EO (Rewopal MPG 40) | " | <0.1 |
| 2-phenoxyethanol | ≦2.4 | 0.04 |
| Benzylalcohol | ≦4 | 0.28 |
| n-hexyldiglycol | ≦1.1 | 0.1 |
| Phenoxypropanol isomer mixture | ≦0.8 | 0.05 |
| Phenylethyl alcohol | ≦2 | 0.08 |
| 3-phenyl-1-propanol | ≦0.6 | 0.5 |

The water miscibility or water solubility of the alcohols is determined by placing 0.2 g alcohol in a 20-ml test tube, mixing it with DM (demineralized) water and vigorously shaking (Vibrofix VE 1 from IKA, maximum speed). If the alcohol has not dissolved after about 5 minutes, it is diluted accordingly with DM water and shaken again. This procedure is repeated until the alcohol has dissolved.

The following dilutions are carried out as standard:

| Alcohol | | Water | Time (shaking) | → | Clear solution |
|---|---|---|---|---|---|
| 0.2 g | + | 0.2 g | 5 minutes | → | >50% |
| 0.2 g | + | 0.8 g | 5 minutes | → | <50 >20% |
| 0.2 g | + | 1.8 g | 5 minutes | → | <20 >10% |
| 0.2 g | + | 3.8 g | 5 minutes | → | <10 >5% |
| 0.2 g | + | 9.8 g | 5 minutes | → | <5 >2% |

If the water miscibility is less than 2%, 0.2 g alcohol are placed in a 200 ml Erlenmeyer flask, diluted with DM water and stirred vigorously for 20 minutes with a magnetic stirrer. If the alcohol has not dissolved, it is diluted accordingly with DM water and stirred afresh.

The following dilutions are carried out as standard:

| Alcohol | | Water | Time (shaking) | Clear → solution | not dissolved |
|---|---|---|---|---|---|
| 0.2 g | + | 19.8 g | 5 minutes | → >2 >1% | |
| 0.2 g | + | 9.8 g | 5 minutes | → <1 >0.5% | |
| 0.2 g | + | 99.8 g | 5 minutes | → <0.5 >0.2% | |
| 0.2 g | + | 199.8 g | 5 minutes | → <0.2 >0.1% | <0.1% |

The time spent stirring or shaking roughly doubles if the visual impression is that the substance could still perhaps dissolve at the existing concentration. The temperature remains disregarded and roughly corresponds to room temperature.

The determination of vapor pressure for the alcohols is carried out in the usual way (see e.g. Ullmans Encyklopadie der technischen Chemie, 4th edition, volume 5, page 88).

The odor threshold value in water represents a further criterion for the alcohols suitable according to the invention. This should be >10, preferably >20 and particularly >50 μmol/l.

Aliphatic glycols of the general formula $R_1$—$(OCH_2$—$CH_2)_n$—$OH$, in which $R_1$ is a straight-chained or branched alkyl group with 2 to 8 carbon atoms, preferably 6 carbon atoms and n is 1 to 4 and preferably 2, have proved to be particularly well suited according to the invention, as have aromatic alcohols. The latter are phenoxyalkanols with more than 2 carbon atoms in the alkyl chain and phenylalkanols, the phenyl ring being optionally substitutable. $C_1$-$C_{18}$ alkyl groups in particular come into consideration as substituents. Examples of such aromatic alcohols are 1-phenoxy-2-propanol, 2-phenoxy-1-propanol, 3-phenoxy-1-propanol, 1-phenoxy-2-butanol, 2-phenoxy-1-butanol, 1-phenylethylalcohol, 2-phenylethylalcohol, 3-phenyl-1-propanol, alpha-4-dimethylbenzylalcohol and mixtures of two or more of these compounds. Examples of aliphatic glycols are n-hexyldiglycol and 2-ethylhexyldiglycol. The use of 3-phenyl-1-propanol and hexyldiglycol has proved to be particularly advantageous (see examples).

The non-ionic surfactants used preferably according to the invention have the general formula $R_2$—$(OCH_2$—$CH_2)_n$—$OR_3$, where $R_2$ is a straight-chained or branched alkyl group with 8 to 18 C atoms, $R_3$ is hydrogen or a straight-chained or branched alkyl group with 1 to 6 carbon atoms and n is 5 to 50. Preferably, a surfactant is used in which $R_2$ has 10 carbon atoms, $R_3$ is hydrogen and n is 8 to 12.

The disinfectant concentrate or disinfectant can contain, as well as the essential components according to the invention given above, usual auxiliaries such as e.g. corrosion protection agents, complexing agents, perfume and/or dyestuffs. It is, however, free from cation-active compounds and nitrogen-containing stabilizers such as e.g. imidazole or imidazole derivatives.

The pH value of the disinfectant concentrates according to the invention is preferably 3 to 6 and in particular 4 to 5.5.

The disinfectant concentrate in general contains 2 to 25 wt. % aldehyde, 2 to 30 wt. % alcohol of limited water miscibility and up to 25 wt. % non-ionic surfactant.

The ready-to-use disinfectant solution in general contains, according to requirements, 1 to 10 wt. % of the concentrate and is obtainable by diluting the concentrate with the corresponding quantity of water. The pH value of the disinfectant solution is between 3 and 7, preferably between 4 and 6. Activation by alkaline additions is not required.

The disinfectant according to the invention is suitable for surface or instrument disinfection, preferably for instrument disinfection with thermolabile materials. It is a clear solution which fulfills the requirements mentioned at the beginning regarding odor development, material compatibility, microbicidal effectiveness and stability in the desired way (see the following examples).

The invention is described in more detail below with reference to examples.

EXAMPLE 1

The increase in action of aldehyde solutions caused by adding alcohols of limited water-miscibility was investigated. The effectiveness against Mycobacterium terrae (ATCC 15755) was determined according to the germ-carrier method according to the guideline for the testing and evaluation of chemical disinfection processes (position at 1.1.81), published in Bbl. Bakt. Hyg., I. Abt. Orig. B 172, 534–562 (1981). In each case 100 g of concentrate were produced which contained 9.00 g glutaraldehyde, 5.00 g succinic dialdehyde, 25.00 g isodecane polyethylene glycol(11) ether (non-ionic surfactant), 10 g of the alcohol to be tested and purified water as the remainder.

The action times required for freedom from germs of the germ carriers with the corresponding use concentrations are noted.

| Disinfectant concentration* | 1% | 2% | 3% |
|---|---|---|---|
| Without addition | >60' | >60' | 60' |
| 3-phenylpropanol-1 | 60' | 15' | 15' |
| Phenylethylalcohol | >60' | 30' | 15' |
| Hexyldiglycol | >60' | 45' | 30' |

*The working solutions employed consisted of the quoted quantity of the disinfectant concentrate and of purified water as the remainder (e.g. 3 g concentrate + 97 g water Δ3%).

Comparison mixtures were further investigated with the alcohols to be tested alone, using the same method. For this, in each case 100 g concentrate were again prepared which contained 20 g of the alcohol to be tested, 20 g tridecane polyethylene glycol(12) ether, 6 g isodecane polyethylene glycol(11) ether and purified water as the remainder. The results reproduced in the following table were obtained.

| Alcohol* | 0.5.% | 1.0% | 2.0% | 3.0% | 5.0% |
|---|---|---|---|---|---|
| Phenoxypropanols | — | — | — | — | — |
| Phenylethanol | — | — | — | — | — |
| 3-phenylpropanol | — | — | — | 120' | 30' |
| Hexyldiglycol | — | — | — | — | — |

— = no sufficient germ reduction within 120 min (">120'")
* = The concentrations given were set by dilution of the concentrates with purified water.

This example shows the surprising increase in action of aldehydic disinfectants caused by adding alcohols of limited water-miscibility, the comparison with the aldehyde-free solutions making it clear that the observed effectivenesses of the mixtures involve a surprising synergism, since the alcohols alone show no effect of their own within a sensible time interval and with acceptable concentrations.

EXAMPLE 2

Example 1 was repeated, using hexyldiglycol in varying quantities as the alcohol of limited water-miscibility. The results reproduced in the following table show the direct dependency of the increase in effect on the quantity of alcohol added.

| Disinfectant concentration | 2% | 3% |
|---|---|---|
| Without addition | >60' | 60' |
| +3% hexyldiglycol | >60' | 45' |
| +10% hexyldiglycol | 45' | 30' |

EXAMPLE 3

Example 1 was repeated, concentrates being produced which contained 18 g glutaraldehyde, 20 g isodecane polyethylene glycol(11) ether (non-ionic surfactant), 20 or 30 g alcohol of limited water-solubility (see table) and purified water as the remainder. The action times necessary for the corresponding concentrations of the working solutions for freedom from germs of the germ-carriers emerge from the following table.

| Disinfectant concentrate | 0.5% | 1% | 1.5% | 2% | 3% |
|---|---|---|---|---|---|
| 30 g triethylene glycol | — | — | — | — | 45' |
| 30 g 1,2-propylene glycol | — | — | — | — | 45' |
| 30 g hexyldiglycol | — | 30' | n.c. | 15' | 15' |
| 20 g hexyldiglycol | — | — | 30' | 30' | n.c. |
| 20 g phenoxypropanol | — | — | 45' | 30' | n.c. |
| 20 g 1-phenylethyl alcohol | — | — | 45' | 45' | n.c. |
| 20 g 3-phenylpropanol-1 | — | 15' | 15' | 15' | n.c. |

— = no effectiveness within 60';
n.c. = not carried out

The tests show that a particularly surprising increase in effect is obtained through the alcohols of limited water-miscibility. Comparable increases in effect were also obtained if succinic dialdehyde or formaldehyde were used in place of or mixed with glutaraldehyde.

EXAMPLE 4

After a longish storage time, concentrates of aldehyde and alcohols show inhomogeneities on the mixing of working solutions with water. In order to investigate this effect, in each case 100 g of concentrate were prepared which contained 5 g succinic dialdehyde, 9 g glutaraldehyde, 20 g isodecane polyethylene glycol(11) ether, 10 g of the alcohol to be tested and 56 g purified water. These formulations were stored for 1 month at +40° C. and then investigated to find at which concentration in water clear solutions were achieved.

| Formulations with alcohol component | Miscibility gap with lower-concentrated solutions than |
|---|---|
| Phenoxypropanol | 7% |
| Phenoxyethanol | 10% |
| Phenethyl alcohol | 14% |
| Hexyldiglycol | no miscibility gap |

It transpires that the limit of water miscibility of the disinfectant concentrate must be below the lowest possible use concentration. The lower the concentration at which separation is observed, the greater the application certainty. These tests further show the surprising stabilizing effect of hexyldiglycols compared with other alcohols with comparable water solubility.

EXAMPLE 5

The stability-increasing action of an addition of an alcohol of limited water solubility is shown by a direct comparison between a disinfectant, found in the market place, based on dialdehydes with 20% ethanol and 15% 1-propanol and a formulation according to the invention which contains, in 100 g, 5 g succinic dialdehyde, 9 g glutaraldehyde, 10 g hexyldiglycol, 25 g isodecane polyethylene glycol(11) ether and otherwise water and a small quantity of corrosion-protection agent. After storing the two formulations at +40° C. over a period of 6 months, the loss of total aldehyde content was determined. With the formulation to be found in the market place the total aldehyde reduction was 13.3 %, whilst the total aldehyde content with the formulation according to the invention decreased by only 4.8%. This comparison shows in particular the stabilizing effect of the alcohol of limited water-miscibility, hexyldiglycol compared with the alcohols ethanol and 1-propanol which have unlimited miscibility with water.

EXAMPLE 6

The particular suitability of hexyldiglycol within the group of the alcohols with limited miscibility is evident in the following test series.

| Mixture | Finding |
|---|---|
| Glutaraldehyde + phenoxyethanol | Miscibility gap or separation |
| Glutaraldehyde + phenoxypropanols | Miscibility gap or separation |
| Glutaraldehyde + benzyl alcohol | Miscibility gap or separation |
| Glutaraldehyde + n-hexyldiglycol | No miscibility gap |

Whilst the first three preparations already showed severe turbidity in the concentrate after a few minutes or hours (particularly with mixtures in the ratio 1:1), the last mixture existed as a clear stable solution even after a period of over 4 months.

Similar results were obtained in corresponding tests with succinic dialdehyde and formaldehyde.

EXAMPLE 7

Concentrate formulations with 5% succinic dialdehyde and 9% glutaraldehyde and 10% hexyldiglycol were stored for 1 month at 40° C. with varying quantities of different non-ionic surfactants and subsequently tested as to whether the 1.5% working solution prepared from it by dilution with water is clear, opal or cloudy.

| | | | | | | | | | Concentrate formulation with |
|---|---|---|---|---|---|---|---|---|---|
| 25 | 22.5 | 20 | 18 | 15 | 12 | 10 | 8 | 5 | 3% isodecane polyethylene glycol(11) ether |
| ←clear→ | | ←opal→ | | ←cloudy→ | | | | | |
| 25 | 22.5 | 20 | 18 | 15 | 12 | 10 | 8 | 5 | 3% isodecane polyethylene glycol(12) ether |
| ←clear→ | | | ←opal→ | | | | | | |
| 25 | 22.5 | 20 | 18 | 15 | 12 | 10 | 8 | 5 | 3% isodecane polyethylene glycol(40) ether |
| ←clear→ | | ←cloudy→ | | | | | | | |

The above results show that the solubility of the working solutions which were prepared after storing the concentrate depends considerably on the type and quantity of the non-ionic surfactant. Thus 8% tridecane polyethylene glycol(12) ether in concentrate sufficed to produce clear working solutions after 1-month storage of the concentrate at 40° C. With isodecane polyethylene glycol (11) ether, 15% were needed and with tridecane polyethylene glycol(40) ether, 18%.

EXAMPLE 8

The material compatibility of the disinfectants according to the invention compared with known instrument disinfectants was investigated by completely immersing standardized test pieces of plastics material and rubber in 10% aqueous solutions and then measuring the swelling (% weight difference) and describing the appearance. The formulations described in example 5 were used. The results are reproduced in the following table.

| | Commercial product | | Invention | |
|---|---|---|---|---|
| Material | Swelling | Appearance | Swelling | Appearance |
| PE | 0.39% | trace yellowy | 0.08% | unchanged |
| PS, clear | 0.34% | trace yellowy | 0.02% | unchanged |
| ABS | 0.59% | trace yellowy | 0.29% | unchanged |
| PMMA | 1.18% | trace reddish | 0.77% | unchanged |
| PA | 6.59% | yellow | 4.7% | yellow-brown |
| PC | 0.17% | bright pink | 0.01% | unchanged |
| PVC, rigid | 0.24% | unchanged | 0.19% | unchanged |
| PVC, flexible | 2.26% | bright yellow/brown | −0.47% | rather yellower |
| EPDM | 1.07% | unchanged | 0.24% | unchanged |
| Silicon | 2.90% | bright pink | 1.56% | unchanged |
| CR | 4.68% | unchanged | 5.01% | unchanged |
| NR P 14 | 4.48% | somewhat darker | 2.94% | unchanged |
| NR P 11 | 2.47% | unchanged | 1.45% | unchanged |
| NBR | 3.00% | unchanged | 2.87% | unchanged |

The tests surprisingly show throughout a lower degree of swelling and less change in the appearance of the test pieces after contact with the formulation according to the invention compared with the commercial product known to have good material compatibility.

The invention has been described in detail with particular reference to preferred embodiments thereof, but it will be understood that variations and modifications can be effected within the spirit and scope of the invention.

We claim:

1. Aqueous disinfectant concentrate consisting essentially of an aldehyde component selected from the group consisting of succinic dialdehyde, glutaraldehyde and mixtures of such aldehydes, and one or more alcohols of limited miscibility in water, said alcohols having a water miscibility of from 0.1 to 2 wt % and a vapor pressure at 20° C. of less than 2 mbar, and being selected from the group consisting of a phenoxy alkanol with more than 2 carbon atoms in the alkyl chain optionally substituted in the phenyl moiety by $C_1$–$C_{18}$ alkyl, a phenyl alkanol optionally substituted in the phenyl moiety by $C_1$–$C_{18}$ alkyl, and an aliphatic glycol of the formula $$R_1-(OCH_2-CH_2)_2-OH$$

in which $R_1$ is a straight-chained or branched alkyl group with to 8 carbon atoms.

2. Disinfectant concentrate according to claim 1, in which the alcohol is an aliphatic glycol in which $R_1$ is a straight-chained or branched alkyl group with 6 carbon atoms.

3. Disinfectant concentrate according to claim 1 in which the alcohol is a phenoxyalkanol with more than 2 carbon atoms in the alkyl chain or a phenylalkanol.

4. Disinfectant concentrate according to claim 1, in which the alcohol is selected from the group consisting of n-hexyldiglycol, 2-ethylhexyldiglycol, phenoxypropanol, phenylethyl alcohol, 3-phenyl-1-propanol and mixtures of such alcohols.

5. Disinfectant concentrate according claim 4 which contains 2 to 25 wt. % aldehyde and 2 to 30 wt. % alcohol with limited miscibility in water.

6. Disinfectant concentrate according to claim 4 which additionally contains up to 25% non-ionic surfactant of the general formula $$R_2-(OCH_2-CH_2)_n-OR_3$$

where $R_2$ is a straight-chained or branched alkyl group with 8 to 18 carbon atoms, $R_3$ is hydrogen or a straight-chained or branched alkyl group with 1 to 6 carbon atoms and n is 5 to 50.

7. Disinfectant concentrate according to claim 6 which has a pH value of 3 to 6.

8. Disinfectant which contains 1 to 10% of the disinfectant concentrate according to claims 4, 5, 6 or 7.

9. Disinfectant according to claim 8 which has a pH value of 3 to 7.

10. Disinfectant according to claim 9 which has a pH value of 4 to 6.

* * * * *